United States Patent
Parsons et al.

(12)

(10) Patent No.: US 6,193,680 B1
(45) Date of Patent: Feb. 27, 2001

(54) INTRATHORACIC CARDIAC COMPRESSION

(75) Inventors: William R. Parsons, 14252 SW. 121$^{st}$ Ave., Tigard, OR (US) 97224; Robert H. Niermeyer, Tigard, OR (US)

(73) Assignee: William R. Parsons, Tigard, OR (US)

( * ) Notice: Subject to any disclaimer, the term of this patent is extended or adjusted under 35 U.S.C. 154(b) by 0 days.

(21) Appl. No.: 09/202,245

(22) PCT Filed: Jun. 18, 1997

(86) PCT No.: PCT/US97/10661

§ 371 Date: Dec. 9, 1998

§ 102(e) Date: Dec. 9, 1998

(87) PCT Pub. No.: WO97/48364

PCT Pub. Date: Dec. 24, 1997

Related U.S. Application Data

(60) Provisional application No. 60/020,048, filed on Jun. 18, 1996.

(51) Int. Cl.$^7$ ..................................................... A61M 29/02
(52) U.S. Cl. ........................ 601/149; 606/192; 606/196; 604/98.02; 604/97.02; 604/99.01
(58) Field of Search ..................................... 601/148–150, 601/153, 41; 600/207; 606/192, 196; 604/96–99

(56) References Cited

U.S. PATENT DOCUMENTS 4,198,963   4/1980   Barkalow et al. .
4,231,365   11/1980  Scarberry .
4,367,747   1/1983   Witzel .
4,471,775   9/1984   Clair et al. .

Primary Examiner—Danton D. DeMille
(74) Attorney, Agent, or Firm—Klarquist Sparkman Campbell Leigh & Whinston, LLP

(57) ABSTRACT

Trans-esophageal cardiac compression is performed during cardiopulmonary resuscitation by introducing into the esophagus a tube (12) having a distal inflatable member, such as a balloon (20). The balloon (20) is positioned in the esophagus (48) at the level of the ventricles of the heart (50). A rapidly cycling pump (16) (such as a compressible bag) is attached to the tube (12), and used to inflate and deflate the balloon (20) on the tube (12). As the balloon (20) inflates, it compresses the ventricles against the sternum (54), increases the transmural pressure across the ventricular wall, and propels blood out of the heart (50) into the aorta and pulmonary arteries. The balloon (20) is inflated and deflated at a rate of approximately 60 cycles to 80 cycles per minute to maintain perfusion of the heart, brain and other vital organs until more definitive therapy can reestablish the contractile activity of the heart. The balloon (20) can be inflated and deflated by a handheld pump (16), or by a rapidly cycling gas pump (100). A particular embodiment of the pump includes a larger volume pump that is driven by a smaller volume drive pump which cycles rapidly to force gas into and out of the balloon.

15 Claims, 4 Drawing Sheets

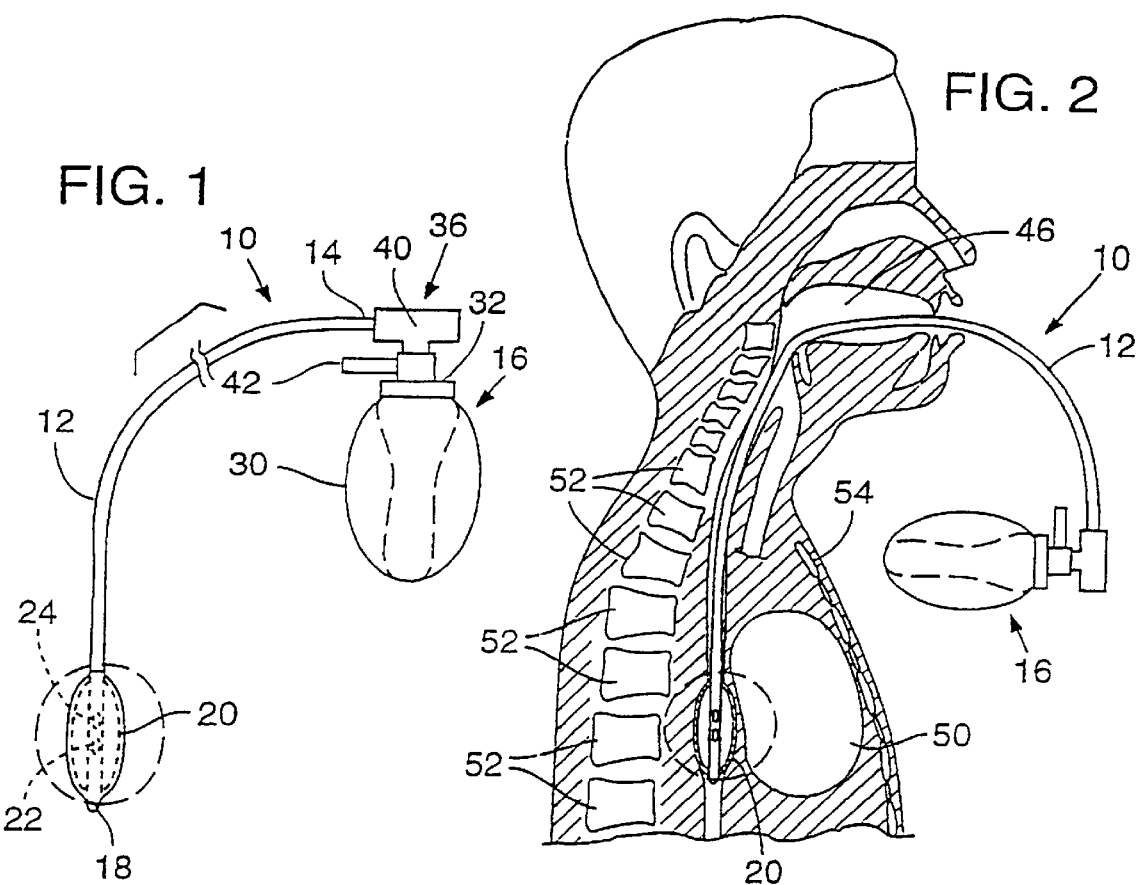
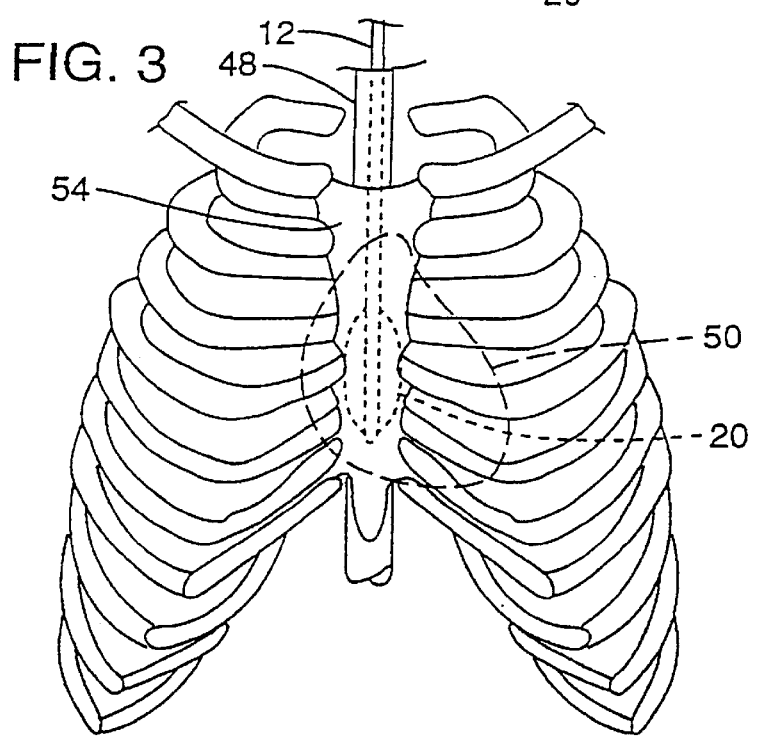

INTRATHORACIC CARDIAC COMPRESSION

This application is a §371 of PCT/US97/10661 filed Jun. 18, 1997 which claims §119(e) of Provisional application 60/020,048 filed Jun. 18, 1996, now abandoned.

FIELD OF THE INVENTION

The present invention relates to methods and devices for performing cardiopulmonary resuscitation, and is more specifically related to intrathoracic cardiac compression during cardiac resuscitation.

BACKGROUND OF THE INVENTION

Cardiopulmonary resuscitation (CPR) is widely used in clinical medicine to maintain perfusion of vital organs during episodes of sudden cardiac arrest when the heart stops spontaneously beating (asystole). Any period of prolonged asystole (such as from ventricular fibrillation) can cause irreversible hypoxic damage to vital end organs (such as the brain and heart) that are not perfused during the asystolic episode. CPR can often maintain a sufficient level of arterial oxygenation and blood flow to avoid irreversible end organ damage and death, at least until spontaneous cardiac activity resumes or external ventricular defibrillation converts the cardiac rhythm to a more effective electrocardiographic pattern.

The components of CPR usually include external cardiac compressions and pulmonary ventilation. The external cardiac compressions are achieved by repetitively forcing the sternum against the heart to compress the heart between the sternum and vertebral column. Manual chest compressions also produce a positive intrathoracic pressure and enhance emptying of the heart, possibly by reducing afterload of the left ventricle. Cardiac compressions are usually only interrupted to administer mouth-to-mouth or mechanical ventilation, which cyclically inflates the lungs to achieve oxygenation of the blood, or to attempt electrical cardioversion of the fibrillating heart.

Although CPR has improved initial survival of episodes of sudden cardiac death, its effectiveness is less than optimal. External compression of the heart, for example, is not as effective as surgically opening the chest and performing direct manual compression of the heart. Several studies have estimated that in-hospital CPR is effective in only 10–15% of patients. Open chest cardiac massage can better achieve normal or supranormal cerebral blood flows, which are associated with improved neurologic recovery from the cardiac event. Such dramatic surgical intervention is not usually available, however, and even in a hospital setting is often impractical or not feasible. The inability of closed chest CPR to maintain adequate levels of cerebral blood flow is the principal reason for the low survival rates and poor neurologic recovery often associated with CPR. Moreover, external chest compressions frequently cause significant morbidity, such as broken ribs or a fractured sternum.

Both external (closed chest) and surgical (open-chest) techniques of cardiac compression can be performed manually, or with the aid of mechanical devices. With either technique, the goal is to maintain artificial circulation, including perfusion of cerebral and coronary arteries, until spontaneous cardiac activity can be restored. An example of an intrathoracic cardiac massager is shown in U.S. Pat. No. 3,496,392, which discloses an inflatable bladder for insertion between the sternum and heart. After intrathoracic placement, the inflatable bladder is cyclically inflated and deflated to achieve cardiac compression.

U.S. Pat. No. 3,233,607, U.S. Pat. No. 3,478,737, U.S. Pat. No. 4,536,893, U.S. Pat. No. 5,119,804 and U.S. Pat. No. 5,383,840 all disclose mechanical devices that surround and engage the ventricular regions of the myocardium to provide auxiliary cardiovascular support for impaired myocardium. U.S. Pat. No. 5,385,081 shows a similar device, but the device is placed in the intrapericardial space. U.S. Pat. No. 5,484,391 describes a substernal heart massaging plunger that is surgically inserted through an intercostal space to compress the heart.

Although these and other heart compressing devices effectively achieve arterial perfusion, they require surgical placement that is often unavailable or impractical in emergency outpatient or clinical settings. Moreover, surgical procedures performed under emergency conditions often inadvertently and unavoidably introduce infectious pathogens into the patient, which can frustrate or prevent recovery.

Other devices have been developed to assist with external cardiac compression, and that avoid the necessity of surgical placement. U.S. Pat. Nos. 5,490,820 and 5,453,081, for example, both disclose external, vest-like devices that are worn by a patient to provide external chest compressions that promote movement of blood from the heart.

None of these devices have been able to provide an approach that combines the effectiveness of intrathoracic cardiac compression with the convenience and availability of external compression devices.

Accordingly, it is an object of this invention to provide an apparatus and method that achieves superior cardiac compression during episodes of ineffective cardiac contraction or asystole.

Yet another object is to provide such an apparatus and method that performs cardiac compression without the necessity of surgical intervention.

These and other objects of the invention will be understood more clearly by reference to the following detailed description and drawings.

SUMMARY OF THE INVENTION

The foregoing problems have been overcome by providing a device for performing intrathoracic transesophageal cardiac compression. The device includes an esophageal tube of suitable size and flexibility to be introduced into the esophagus. An inflatable compression member (such as a balloon) is provided on the esophageal tube. The esophageal tube is of sufficient length to allow the inflatable member to be introduced into the esophagus to a distance that disposes the inflatable member between the heart and vertebral column. The inflatable member has sufficient volume to compress the heart an effective volume (for example 200 cc) to perform therapeutically effective transesophageal cardiac compressions during CPR. A pump connected to the esophageal tube cyclically inflates and deflates the inflatable compression member at a sufficient frequency to restore adequate circulatory blood flow.

In a disclosed embodiment, the inflatable member is a distensible bladder or balloon that can expand to a volume of approximately 200–250 cc. The pump may be a hand-held resilient collapsible and expandable pumping chamber that is compressed to expand the inflatable member, and allowed to expand to deflate the inflatable member. The hand-held pump includes a check valve that allows air to be drawn into the pumping chamber if the pressure in the chamber exceeds a preselected negative value, and allows air to be expelled from the pumping chamber if pressure in the chamber exceeds a preselected positive pressure. Alternatively, the pump can be a rapidly cycling electrically powered or hydraulic actuated air pump. Another alternative method of cyclical inflation of the esophageal balloon is the use of a bottle of compressed air with a pressure regulated valve.

In one embodiment, the rapidly cycling pump includes a reciprocating pump piston that defines a variable volume gas chamber, the volume of which is varied by movement of the pump piston. The pump piston is driven by a separate drive piston, which is reciprocated in response to a hydraulic signal that can be rapidly changed to cycle the pump at the desired frequency. A delay mechanism can prolong the pumping cycle, for example by interposing a delay of approximately 250–300 milliseconds, between deflation and inflation of the esophageal balloon. This delay allows end diastolic filling of the heart to take place more efficiently than would occur if the pump constantly cycled without a pause between inflation and deflation of the balloon.

The invention also includes a method of performing transesophageal cardiac compressions by providing the inflatable member on an esophageal tube, and then introducing the inflatable member into the esophagus a sufficient distance to dispose the inflatable member between the heart and vertebral column. The inflatable member is then cyclically inflated and deflated a sufficient volume (for example 200 cc) at a sufficient rate (for example 40–80 cycles per minute, preferably 60–80 cycles per minute) to compress the heart during CPR. The inflatable member is preferably positioned at the level of the ventricles, such that expansion of the inflatable member compresses the ventricles against the sternum to expel blood into the aorta. Subsequent deflation of the member allows the ventricles to expand, which draws blood into the heart for subsequent circulation secondary to venous pressure and blood flow from the superior and inferior vena cava via the right auricle.

BRIEF DESCRIPTION OF THE DRAWINGS

FIG. 1 is a view of the cardiac compression device of the present invention, portions of the tubing being broken away for purposes of illustration.

FIG. 2 is a schematic view, in sagittal section through the head and thorax, illustrating the position of the cardiac compression device in use.

FIG. 3 is a front view of the thorax, illustrating the desired placement of the compression device.

DETAILED DESCRIPTION OF PREFERRED EMBODIMENTS

Figure 4:
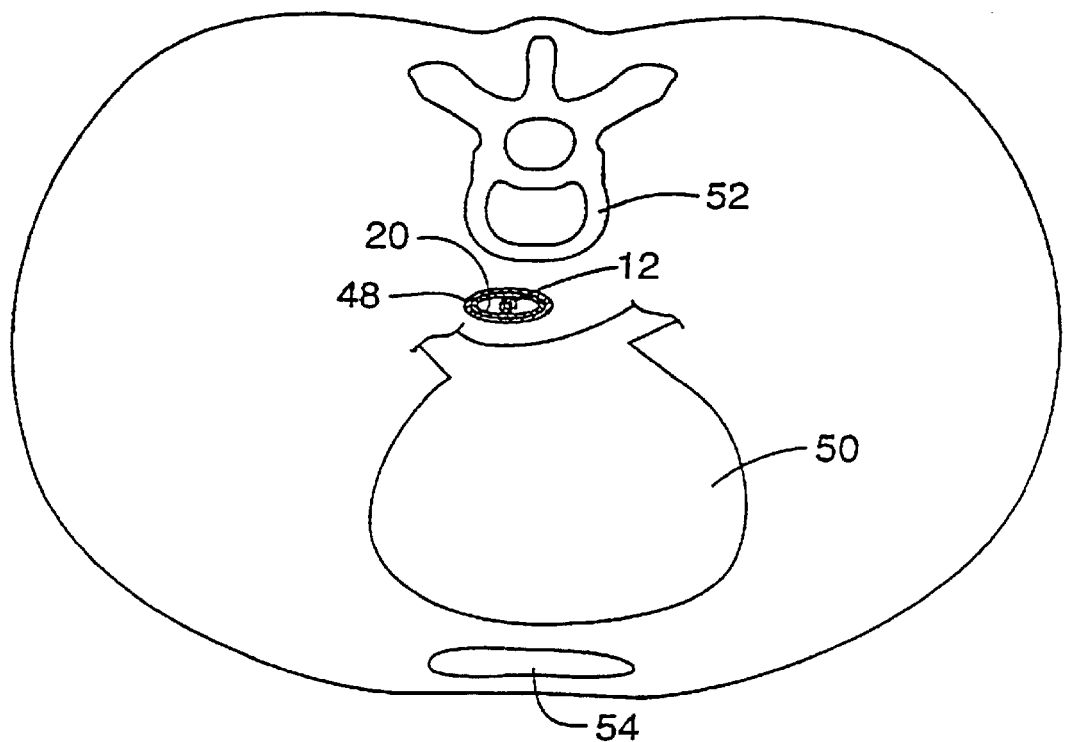
FIG. 4 is a transverse schematic sectional view through the thorax, at the level of the ventricles, illustrating placement of the cardiac compression device.

A device 10 for performing transesophageal cardiac compression during CPR is shown in FIG. 1 to include an esophageal tube 12 of suitable size and flexibility to be introduced into the esophagus. Such a tube may be a large bore nasogastric tube (for example 18–24 French plastic tubing) or a 15 mm diameter endotracheal tube. The tube 12 may be of varying lengths, but is preferably at least 40 cm long. A portion of the tube 12 in FIG. 1 is cut away for purposes of depiction, but the actual tube is a clear plastic member with a continuous cental bore therethrough.

Tube 12 has a proximal end 14 that is connected to a pump 16, and a distal end 18 that is provided with an inflatable member 20. The inflatable member 20 is a balloon or distensible bladder that is sealed circumferentially to tube 12 above and below a pair of orifices 22, 24 that communicate with the continuous bore of the tube. Air in the tube communicates with the interior of the sealed balloon through the orifices 22, 24.

The pump 16 is a hand-held resilient collapsible and expandable chamber pump, such as a conventional ambulatory ventilation bag 30. The bag 30 is made of a resilient collapsible and expandable material that encloses an air chamber of variable volume. Bag 30 extends between and is suspended by a pair of opposing structural end members 32, 34. Member 32 is a solid plastic or metal top cap that supports an air control mechanism 36 (described below), while member 34 is a solid or ring shaped bottom. The variable volume of bag 30 is illustrated in FIG. 1, wherein the expanded volume of the bag 30 is shown in solid lines, and a compressed condition of the bag is illustrated in phantom lines. Bag 30 is compressed manually, for example by squeezing the bag at a middle section to decreases the volume of the enclosed chamber, and expel air from the chamber.

Air control mechanism 36 includes a generally L-shaped connector 40 that communicates at one end with the interior of bag 30 and at the other end with flexible tube 12. The L-shape of connector 40 allows the bag 16 to be held in a comfortable position relative to tube 12 during use when the patient is in a supine position. A check valve 42 communicates with connector 40, and allows air to be drawn in through valve 42 when a negative pressure in bag 30 exceeds a preselected value, and allows air to be expelled through valve 42 when a positive pressure in bag 30 exceeds a preselected value. As long as pressures in bag 30 are within the preselected range, all air flow occurs through connector 40 into tube 12.

The device 10 is used during CPR to provide intrathoracic transesophageal cardiac compressions. In use, the device 10 is provided with the balloon 20 in its deflated condition. Pump 16 may be attached to the tube prior to insertion of the tube 12 into the esophagus, or attached to the tube subsequent to insertion. With the patient in the prone position, an estimate of the length of tube needed to position the balloon 20 can be made by placing the balloon externally on the chest at the level of the xiphoid and determining the length of tube that reaches from the xiphoid to the lips of the patient. Then the mouth is opened and the distal tip 18 of the tube is advanced into the posterior oropharynx 46 (FIG. 2) and then into the esophagus 48. Advancement of the tube is continued until the tube is advanced the estimated predetermined length, at which position the balloon is positioned in the esophagus 48 between the heart 50 and one or more vertebrae 52 of the spinal column. A preferred position of the balloon 20 is shown in the front view of FIG. 3, wherein the balloon is positioned at the level of the ventricles of the heart. The sternum 54 is shown anterior to the heart in FIGS. 2 and 3.

Once the balloon is in its desired position, and pump 16 is attached to tube 12, the resilient bag 30 of pump 16 is manually grasped and compressed. The compressed condition of the bag 30 is shown in broken lines in FIG. 1. As the bag 30 is compressed, pressure in the bag is increased and air is expelled out of pump 16, into tube 12, through holes 22, 24, and into the balloon 20. Air is expelled from bag 30 as it is collapsed, which fills the balloon 20 to the shape shown in broken lines in FIGS. 1 and 2. In the preferred embodiment, bag 30 in compressed to expel a sufficient volume of air to fill balloon 20 to a volume of approximately 200 cc or more. The 200 cc volume of the inflatable member is selected because that is the approximate stoke volume of a normal heart during systole.

Balloon 20 is then subsequently deflated to its original volume by releasing pressure that was exerted on bag 30. The resilient bag expands to its original volume, which creates a negative pressure in bag 30 to draw air out of the inflatable member and into the bag 30. The balloon 20 is thereby deflated to its residual volume.

Figure 5:
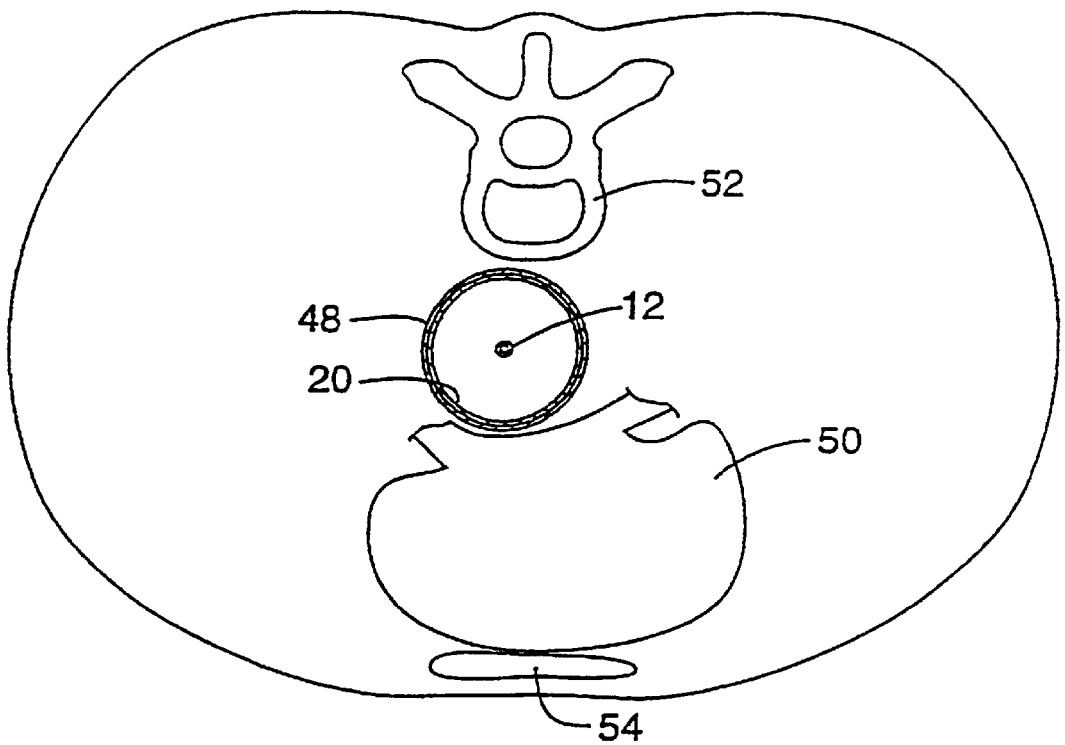
FIG. 5 is a view similar to FIG. 4, but showing the cardiac compression device in an inflated condition.

The transesophageal action of the inflatable member is shown in the transverse thoracic sections of FIGS. 4 and 5. In FIG 4, the balloon 20 (in the deflated condition) is positioned at the level of the ventricles between vertebra 52 and heart 50. This view shows the sternum immediately anterior to the heart. The balloon 20 is expanded by compressing bag 30 of pump 16 (FIGS. 1 and 2), which expands the distensible esophagus to a volume of at least about 200 cc, as shown in FIG. 5. This enlarged esophageal volume expands to fill an area between vertebra 52 and heart 50, and compresses the ventricles of heart 50 between balloon 20 and sternum 54. Compression of the ventricles forces blood into the aorta and coronary arteries for perfusion of vital organs. Expansion and contraction of the balloon 20 is cyclically repeated, for example at 60–80 cycles per minute, to continue perfusion of vital organs until the heart can resume it rhythmic activity.

Although the embodiment of this specification operates with a hand compressed bag, any other convenient means can be used to cyclically inflate and deflate the balloon 20. A rapidly cycling centrifugal or piston pump may, for example, be substituted for the bag 30.

Figure 6:
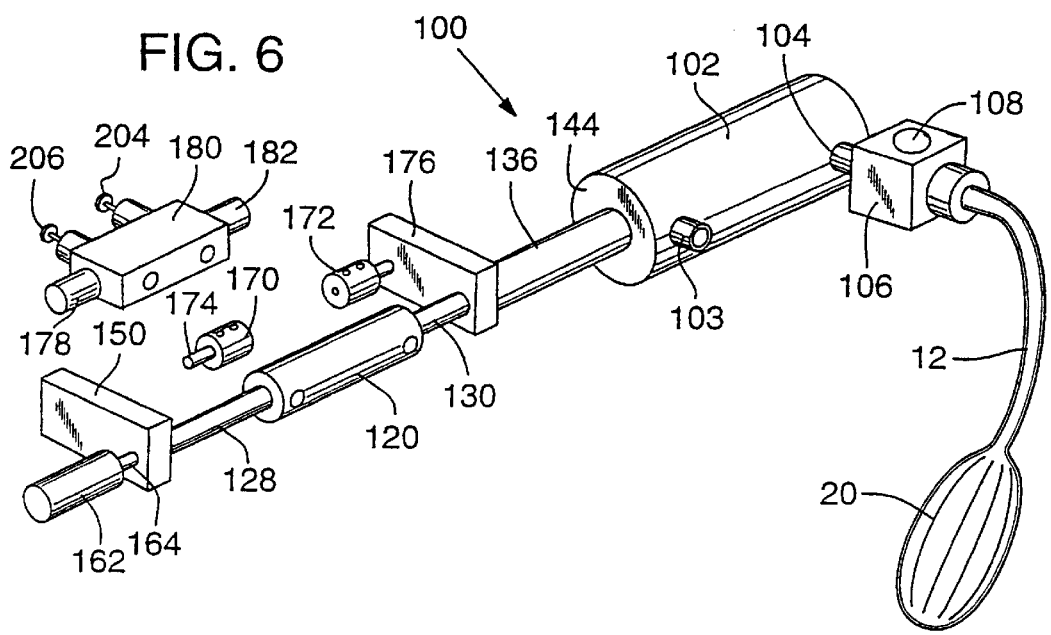
FIG. 6 is a perspective view of portions of an embodiment of a rapidly cycling pump that is used to inflate and deflate the cardiac compression device.
Figure 7:
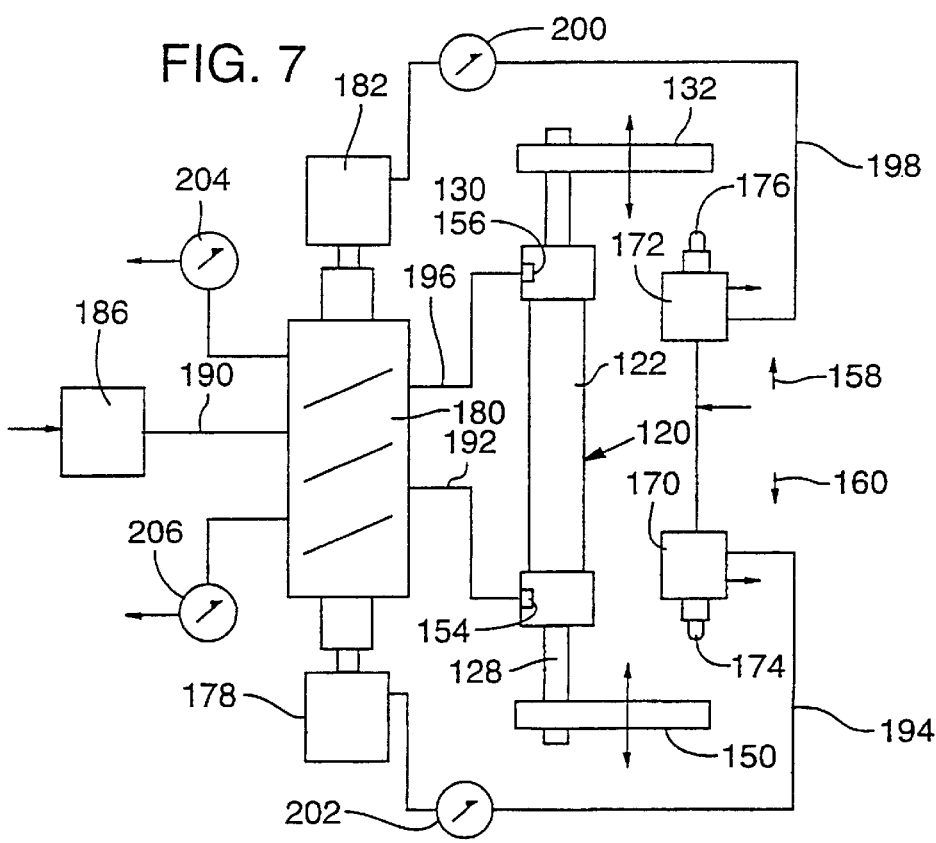
FIG. 7 is a schematic view of the hydraulic system that controls the drive pump of FIG. 6.
Figure 8:
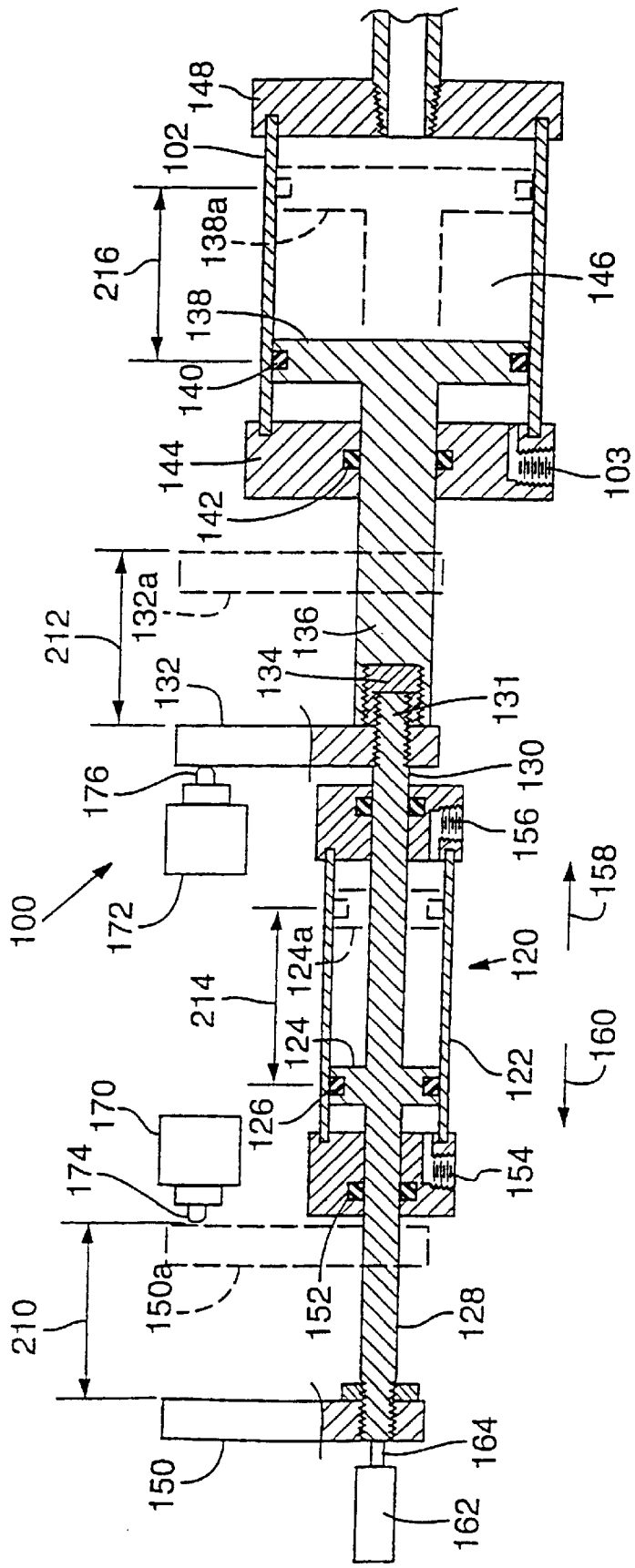
FIG. 8 is a cross-sectional view of the pump taken along line 8—8 in FIG. 6, and wherein advanced positions of pump components are shown in phantom lines.

A particular embodiment of a pump 100 that is suitable for automatically inflating and deflating the bag is shown in FIGS. 6–8. Pump 100 (FIGS. 6 and 8) includes a large diameter air (or other gas) container, which in the disclosed embodiment is a cylinder 102 having a vent 103 to the atmosphere, and a coupling 104 connecting the cylinder 102 to a pump replenish valve 106. Valve 106 has a vent 108 for selectively introducing additional air (or other gas) into the pumping system if it is needed. Valve 106 is in turn connected to the tube 12 of the resuscitation device 10, so that pump 100 can introduce air into, and remove air from, inflatable member 20.

Pump 100 is driven by a drive pump 120 that is illustrated in FIGS. 6–8. The pump 120 includes a drive cylinder 122 within which can reciprocate an enlarged piston head 124 (FIG. 8) having a peripheral seal 126. A rear piston rod 128 extends through the rear face of cylinder 122, an a front piston rod 130 extends through the front face of cylinder 122. Front rod 130 has an externally threaded tip 131 that is fixed to a front lever plate 132, which plate extends perpendicular to the longitudinal axis of rod 130. Threaded tip 131 extends through plate 132 to engage an internally and externally threaded adaptor 134 that engages an internally threaded end of a larger diameter piston rod 136 that drives a piston head 138 in pump cylinder 102. A peripheral seal 140 around piston head 138 establishes a fluid tight relationship between piston head 138 and the walls of cylinder 102, while an internal seal 142 in front wall 144 of cylinder 102 maintains a gas tight relationship between piston rod 136 and wall 144.

A pumping chamber 146 is defined within cylinder 102 between piston head 138 and a front wall 148 of the cylinder. Chamber 146 contains a desired volume of gas (for example 250 cc) when the piston head 138 is in the fully retracted position shown in solid lines in FIG. 8. The volume of chamber 146 can be varied by moving piston head 138 between the position shown in solid lines in FIG. 8, and the advanced position shown in phantom lines and designated 138a. Reducing the volume of pumping chamber 146 expels a volume of gas proportional to the stroke of the piston head 138 (e.g. 200 cc) out of chamber 146 and into the cardiac compression device.

A rear lever plate 150 is fixed to the threaded tip of rear piston rod 128, such that plate 150 extends perpendicular to the longitudinal axis of piston rod 128. A seal 152 between rear piston rod 128 and the wall of drive cylinder 122 prevents gas in cylinder 122 from escaping. A forward gas coupling 154 communicates with the interior of cylinder 122 behind piston head 124, while a reverse gas coupling 156 communicates with the interior of cylinder 122 forward of piston head 124. Hence gas introduced through forward coupling 154 drives piston head 124 and its associated rods 128, 130 in the forward direction 158, while gas introduced through reverse coupling 156 drives piston head 124 and its associated rods in the reverse direction 160.

A shock absorber 162 (FIGS. 6 and 8) is positioned in the path of movement of rear lever plate 150 so that plate 150 hits a pin 164 of the shock absorber near the fully reverse position of plate 150, shown in solid lines in FIG. 8. The shock absorber slows the velocity of the reverse movement of the drive pump piston, and therefore introduces a short delay between the reverse movement of the drive piston 124 and its subsequent forward movement. This delay provides a pause between pumping cycles to allow better end diastolic filling of the heart, as explained below.

As illustrated in FIGS. 6–8, a rear three way poppet valve 170 is positioned at the forward end point of the path of movement of rear plate 150, designated 150a in phantom lines in FIG. 8. A front three way poppet valve 172 is also positioned at the rearward end point of the path of movement of front plate 132. Hence rear plate 150 depresses an actuator 174 of valve 170 when piston 124 of drive pump 120 has moved to its forwardmost desired position, and plate front 132 depresses an actuator 176 of valve 172 when piston 124 has moved to its rearwardmost desired position. Actuation of rear valve 170 sends a pulse of 80 psi gas to a rear remote activator 178 of a five way valve 180. Alternate actuation of front valve 172 sends a pulse of 80 psi gas to a front remote actuator 182. The volume of the pump is set by the placement of valves 170 and 172, which determine the stroke of piston 124.

In operation, gas is supplied through a regulator 186 (FIG. 7) to valve 180 through line 190. The supplied gas may be oxygen from an oxygen tank of the type used in hospitals and emergency vehicles, and may be supplied at a pressure of 80–3000 psi. The gas is supplied at a pressure of 80 psi in the disclosed embodiment. The pressure at which the gas is supplied to valve 180 helps determine the speed with which the pump operates. Higher pressures increase the speed with which the pump cycles, and in turn increases the frequency of cardiac compressions delivered to the patient.

The five-way valve 180 is in a position to allow the gas to move through line 192 and into forward coupling 154 to start the pumping cycle. Piston 124 in drive cylinder 122 (FIG. 8) is pushed in the forward direction 158, which in turn advances rod 136 and piston head 138 in large pump cylinder 102 in forward direction 158. As piston head 138 advances, approximately 200 cc of air is pushed out of cylinder 102 into tube 12 and pumping member 20 within the esophagus. Forward motion of piston head 138 is stopped at the position designated in phantom lines as 138a, when rear plate 150 reaches the position shown as 150a and pushes actuator 174 to activate rear valve 170. When rear valve 170 is actuated, it sends an 80 psi pulse of gas through line 194 to the rear remote activator 178. This pulse of gas shifts the five way valve 180 such that gas being supplied through line 190 is now directed through line 196 instead of line 192.

Gas directed through line 196 moves through reverse coupling 156 into cylinder 122 forward of piston head 124 when piston head 124 is in the position when in phantom as 124a. The drive piston therefore moves rearwardly in the direction 160, which in turn moves piston 138 in the reverse direction 160 within cylinder 102, and opens valve 170 to vent activator 178. As piston 138 retracts, it pulls air out of compression member 20 to deflate it, and allow the heart to expand. Near the end of the reverse stroke of piston head 124, rear plate 150 contacts pin 126 of shock absorber 130 to slow the velocity of the reverse stroke, which adds some time (for example a few hundred milliseconds) to the cycle before the cycle starts again.

At the selected end point of the reverse stroke of drive pump 120, front plate 132 contacts actuator 176 of front valve 172, which sends an 80 psi pulse of gas through line 198 to the front remote activator 182. This pulse of gas shifts valve 180 so that the supply gas is again directed through line 192, and the pumping cycle begins again. This arrangement allows the gas pump 100 to be cycled rapidly (e.g. 60–100 cycles per minute) to deliver the appropriate number of compressions to the patient's heart).

A delay needle valve 200 may be interposed in line 198 to change the speed at which actuation of valve 172 changes the position of valve 180. Similarly a delay needle valve 202 may be interposed in line 194 to change the speed at which actuation of valve 170 changes the position of valve 180. The delay valves 200, 202 may therefore be used to control the cycle speed of the pump, which in turn controls the frequency of cardiac compressions. Velocity control needle valves 204, 206 on five-way valve 180 may also be used to control the velocity of drive pump cycles.

In the disclosed embodiment, cylinder 102 is a 2.5 inch (6.5 cm) diameter cylinder that holds a maximum of 250 cc gas in pumping chamber 146. Cylinder 122 is a ¾ inch (2 cm) diameter cylinder. The stroke cycle produced by this pump is divided into approximately thirds, with about ⅓ of the cycle being a forward stroke to pump gas into the pumping member 20 to compress the heart, about ⅓ of the cycle being a return stroke to draw gas out of the pumping member to allow the heart to expand, and about ⅓ of the cycle being a pause to allow the heart to fill with blood during end diastole. In a disclosed embodiment, the period of delay is at least 250 milliseconds, for example 250–300 milliseconds. This type of cycle imitates the pumping action of the human heart, in which end diastolic filling is allowed to occur before another contraction of the heart begins.

The stroke volume of pump cylinder 102 is set by the position of three-way valves 170, 172. Moving the valve 170 in the direction 160 (FIG. 8) shortens the paths of movement 210 and 212 of plates 132 and 150, and the strokes 214 and 216 of piston heads 124 and 138, because path of movement 210 of plate 150 will be shorter before actuator 174 is activated to start the reverse stroke. The stroke can similarly be lengthened by moving valve 170 in the direction of arrow 158. Valve 172 can similarly be positioned to alter the position at which plate 132 actuates valve 172 to reverse the pump cycle.

If desired, inflation and deflation of the balloon 20 may be interrupted to intermittently ventilate the patient. Alternatively, ventilations may be carried out concurrently with cardiac compressions to take advantage of intrathoracic pressure fluctuations that assist in pumping blood from the heart.

As used in this specification, the term "fluid" includes a gas or liquid.

Having illustrated and described the principles of the invention in several preferred embodiments, it will be apparent to those skilled in the art that the invention can be modified in arrangement and detail without departing from such principles.

We claim:

1. A method of performing intrathoracic transesophageal cardiac compression, comprising: providing a inflatable member on an esophageal tube; introducing the inflatable member into the esophagus a distance that disposes the inflatable member between the heart and vertebral column; cyclically inflating and deflating the inflatable member a sufficient volume at a sufficient rate to compress the heart and perform therapeutically effective transesophageal cardiac compression.

2. The method of claim 1, wherein inflating the inflatable member comprises introducing at least 200 cc of a fluid into the inflatable member.

3. The method of claim 1, further comprising performing pulmonary resuscitation.

4. The method of claim 1, wherein cyclically inflating and deflating the inflatable member at a sufficient rate comprises inflating and deflating the inflatable member at a rate of at least about 60 cycles per minute.

5. The method of claim 1, wherein cyclically inflating and deflating the inflatable member at a sufficient rate comprises inflating and deflating the inflatable member at a rate of at least about 60 cycles per minute.

6. The method of claim 1, wherein cyclically inflating and deflating the inflatable member further comprises pausing between pumping cycles a sufficient period of time to allow end ventricular end diastolic filling to occur.

7. The method of claim 1, wherein cyclically inflating and deflating the inflatable member comprises moving gas into and out of the inflatable member from a pump gas container having a reciprocable piston, and the reciprocable piston is reciprocated by a separate drive piston.

8. A device for performing intrathoracic transesophageal cardiac compression, comprising:

an esophageal tube of suitable size and flexibility to be introduced into the esophagus;

an inflatable member on the esophageal tube, wherein the esophageal tube is of sufficient length to allow the inflatable member to be introduced into the esophagus a distance that disposes the inflatable member between the heart and vertebral column, and the inflatable member has a sufficient volume to compress the heart an effective volume to perform therapeutically effective transesophageal cardiopulmonary resuscitation; and a pump connected to the esophageal tube, wherein the pump cycles sufficiently rapidly to inflate the inflatable member at a sufficient frequency to perform therapeutically effective cardiopulmonary resuscitation, wherein the pump is an automatic pump that cycles a volume of gas of at least 200 ccs, at least 40 cycles per minute.

9. The device of claim 1, wherein the pump comprises a hand-held resilient collapsible and expandable pumping member that is compressed to expand the inflatable member, and allowed to expand to deflate the inflatable member.

10. The device of claim 1, wherein the pump comprises a pumping container for containing a volume of gas, and connections for transferring gas into and out of the pumping member.

11. The device of claim 10 further comprising a drive piston that is reciprocated by fluid pressure to reciprocate a pumping piston within the pumping container.

12. The device of claim 10, further comprising a delay mechanism that prolongs a period of removal of the gas from the pumping member as compared to a period of introduction of the gas into the pumping member.

13. The device of claim 11, wherein the drive piston is included in a drive pump comprising a cylinder in which the drive piston reciprocates, and the drive piston moves in response to differential fluid pressure on opposing faces of the drive piston to move the drive piston and pumping piston in a first direction and introduce fluid into the pumping member, and to move the drive piston and pumping piston in a second direction and withdraw fluid from the pumping chamber.

14. The device of claim 13, further comprising a shock absorber against which the drive piston impacts as the drive piston reciprocates to draw fluid out of the pumping container, to introduce a delay between drawing fluid out of the inflatable member and transferring fluid out of the inflatable member.

15. The device of claim 1 wherein the inflatable member has a volume capacity, when inflated, of at least 200 cc.

* * * * *

UNITED STATES PATENT AND TRADEMARK OFFICE
CERTIFICATE OF CORRECTION

PATENT NO. : 6,193,680 B1 Page 1 of 1
DATED : February 27, 2001
INVENTOR(S) : William R. Parsons It is certified that error appears in the above-identified patent and that said Letters Patent is hereby corrected as shown below:

<u>Column 8,</u>
Lines 40-43, delete claim 5.

Signed and Sealed this

Twenty-fifth Day of March, 2003

JAMES E. ROGAN
*Director of the United States Patent and Trademark Office*